US00RE37964E

(19) United States
(12) Reissued Patent
Prats et al.

(10) Patent Number: US RE37,964 E
(45) Date of Reissued Patent: Jan. 7, 2003

(54) FEMORAL PROSTHESIS EMPLOYING A SMALL CERAMIC BALL

(75) Inventors: Christian Prats, Valenciennes (FR); Pierre Vivier, Paris (FR)

(73) Assignee: Ceramiques Techniques Desmarquest (FR)

(21) Appl. No.: 08/375,086

(22) Filed: Jan. 19, 1995

Related U.S. Patent Documents

Reissue of:
(64) Patent No.: 5,181,929
Issued: Jan. 26, 1993
Appl. No.: 07/497,625
Filed: Mar. 23, 1990

(30) Foreign Application Priority Data

Mar. 23, 1989 (FR) ..... 89 04431

(51) Int. Cl.[7] ..... A61F 2/24
(52) U.S. Cl. ..... 623/23.11
(58) Field of Search ..... 623/23.11, 22.11

(56) References Cited

U.S. PATENT DOCUMENTS

| | | | | |
|---|---|---|---|---|
| 4,012,795 A | | 3/1977 | Dorre et al. | |
| 4,058,856 A | | 11/1977 | Doerre et al. | |
| 5,047,062 A | * | 9/1991 | Pappas et al. | 623/23 |
| 5,413,610 A | | 5/1995 | Amino et al. | |

FOREIGN PATENT DOCUMENTS

JP 62-111013 7/1987

OTHER PUBLICATIONS

T. Tateishi and H. Yunoki, "Research and Development of Advanced Bio–Composite Materials and Application to the Artificial Hip Joint", Bulletin of Mechanical Engineering Laboratory—Japan, No. 45, 1987, pp. 1–9.

P. Christel, A. Meunier, and M. Heller of the Laboratoire de Recherches Orthopediques and J. P. Torre and C. N. Peille of Ceramiques Techniques Desmarquest, "Mechanical properties and short–term in–vivo evaluation of yttrium–oxide–partially–stabilized zirconia", Journal of Biomedical Materials Research, vol. 23, 45–61 (1989).

H. Fessler and D. C. Fricker, "A study of stresses in alumina universal heads of femoral prostheses", Proc. Instn. Mech. Engrs., vol. 203, 15–34 (1989).

P. Christel, A. Meunier, J. M. Dorlot, J. M. Crolet, J. Witvoet, L. Sedel and P. Boutin, "Biomechanical Compatibility and Design of Ceramic Implants for Orthopedic Surgery", Annals New York Academy of Sciences, pp. 234–256.

Gunther Heimke, "The Safety of Ceramic Balls on Metal Stems in Hip Arthroplasty", Adv. Mater. 1994, 6, No. 2, pp. 165–170.

H. Fessler and D. C. Fricker, "Friction in femoral prosthesis and photoelastic model cone taper joints", Proc. Instn. Mech. Engrs., vol. 203, 1–14 (1989).

G. Schwartz, C. A. Dingman, and J. A. Davidson, "Effect of Trunnion Angle on the Static Strength and Stress Distribution in Ceramic Femoral Heads", The Third World Biomaterials Congress, Apr. 21, 1988, Kyoto, Japan, p. 438.

Smith & Nephew Richards Inc., Zirconia Ceramic Technical Monograph, "The Next Generation of Ceramics—Zirconium Oxide Ceramic Femoral Heads", pp. 1–16.

(List continued on next page.)

*Primary Examiner*—David J. Isabella
(74) *Attorney, Agent, or Firm*—Nixon Peabody LLP

(57) ABSTRACT

The disclosure relates to a femoral prosthesis consisting of a metal rod having a male frustoconical end portion and a femoral head, or ceramic ball, having a frustoconical blind recess, assembled by means of a conical sleeve fitment. The ceramic ball is formed of material having an improved flexion breakage modulus and an improved elasticity modulus.

1 Claim, 2 Drawing Sheets

OTHER PUBLICATIONS

Figure 1:
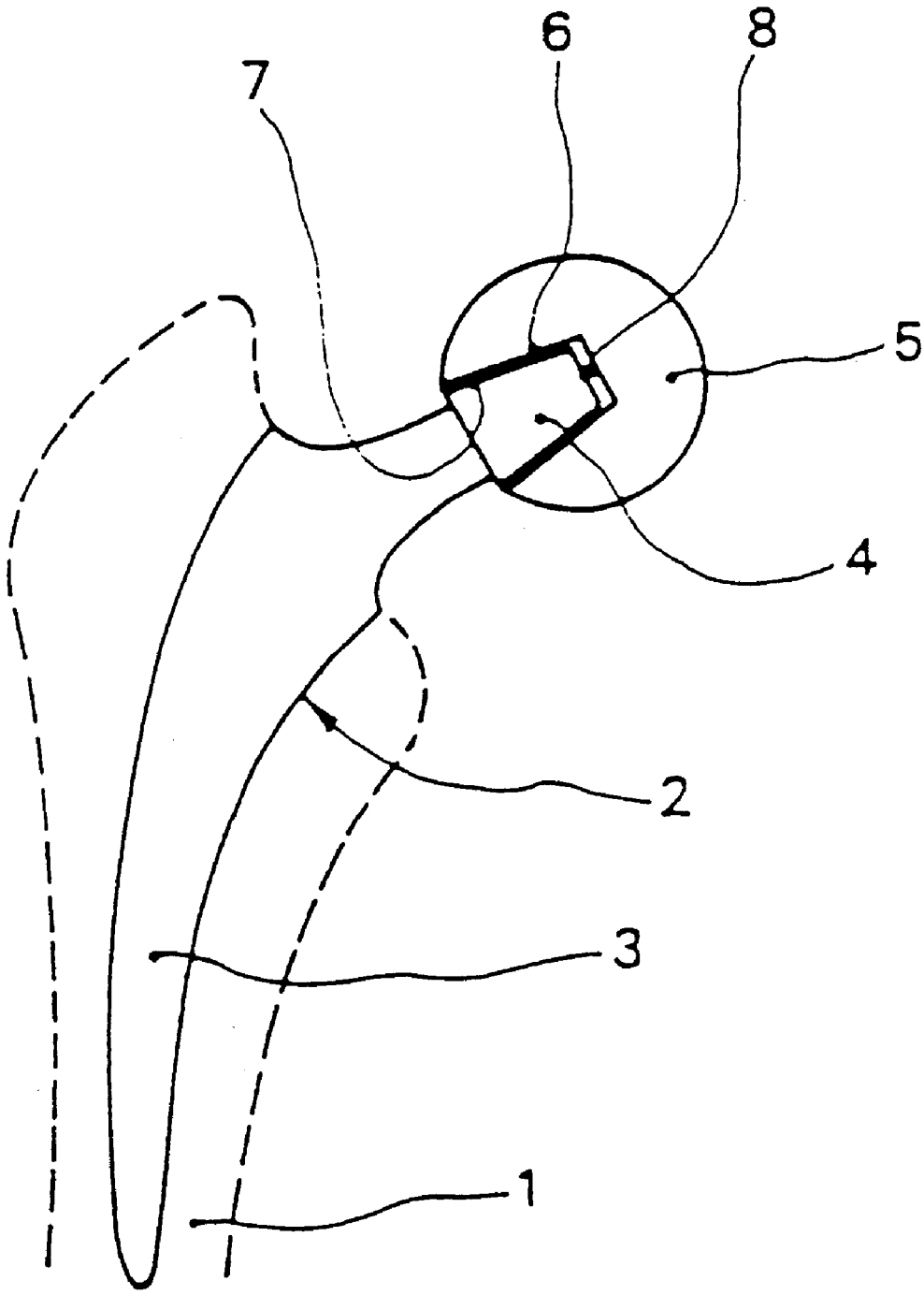

M. Kilvington and R. M. F. Goodman, "In vivo hip joint forces recorded on a strain gauged 'English' prosthesis using an implanted transmitter", Engineering in Medicine, MEP Ltd., 1981, vol. 10, No. 4, pp. 175–187.
R. A. Wordsworth and B. Weightman, "Laboratory development of a method of attaching ceramic femoral heads to metal stems", Biomaterials 1986, vol. 7, Mar., pp. 83–88.
A. Sudanese, A. Toni, G. L. Cattaneo, D. Ciaroni, T. Greggi and D. Dallari, "L'ossido di zirconio . . . ", Chir. Org. Mov., LXXIII, 195–198, 1988.
Sudanese et al., Alumina vs Zirconium Oxide: A comparative Wear Test. In Oonishi H. Aoki M, Sawai L (eds) Bioceramics 1989, pp. 237–240.
Bioceramics: Materials and Applications, Articulation Components Out of Ceramics For Total Hip Replacement:, Gerd Willmann, Proceedings of the Biomedical and Biological Applications of Ceramics and Glass Symposium, presented at the 96th Annual Meeting of the American Ceramic Society, held in Indianapolis, IN, Apr. 25–27, 1994, and the Workshop on Ceramics for Biomedical Applications, held in Alfred, NY, Jun. 8–10, 1994, pp. 83–89.
Ceramics in Substitutive and Reconstructive Surgery, 1991, "Wear Behaviour of Different Ceramic Surfaces in Comparison to TiN and OHD–Treated Ti–6A1–7Nb Alloy Paired with Polyethylene", R. M. Streicher, H. Weber, R. Schon, M. Semlitsh, pp. 197–205.
Proceedings of the International Symposium on Advanced Ceramics for Structural and Tribological Applications—Honouring A.C.D. Chaklader, Emeritus Professor, Vancouver, British Columbia, Aug. 20–24, 1995, Advanced Ceramics for Structural and Tribological Applications, "Possibilities and Limits of Wear Protection Through Advanced Ceramics", K. H. Habig. pp. 389–400.
Proceedings of the International Symposium on Advanced Ceramics for Structural and Tribological Applications–Honouring A.C.D. Chaklader Emeritus Professor, Vancouver, British Columbia, Aug. 20–24, 1995, Advanced Ceramics for Structural and Tribological Applications, "Designing for Effective Use of "debris" in Wearing Systems: With an Illustration From Ceramic Wear", K. C. Ludema, pp. 37–45.
Mat. Res. Soc. Symp. Proc. vol. 78. 1987 Materials Research Society, "Evaluation of Commercially Available Transformation Toughened Zirconia", Jeffrey J. Swab, pp. 137–146.
Prozyr, C. T. Desmarquest, The Future of Implantology, "Sterilization and Long Term Ageing of Prozyr in Ringer's Solution", B. cales and Y. Stefani, 1992, pp. 19–23.
Ceramic Raw Materials, Edited by D.J.DeRenzo, copyright 1987, "Zirconia (Zirconium Oxide)", pp. 553–587.
Advanced Ceramic Materials, Technological and Economic Assessment, Copyright 1995, "Assessment of the International Competitiveness of the Advanced Ceramics Industry", pp. 518, 523, 540, 573.
Communications of the American Ceramic Society, Oct. 1986, J. Am. Ceram. Soc., 69 [10] C–224–C–226 (1986), Ferroelastic Domain Switching as a Toughening Mechanism in Tetragonal Zirconia, Anil V. Virkar and Roger L. K. Matsumoto.
Dr.–Ing. Richard Ernst, Comprehensive Dictionary of Engineering and Technology, vol. X, English–French, p. 955 and 1250.
Guidance Document For the Preparation of Premarket Notifications For Ceramic Ball Hip Systems, Apr. 27, 1989, pp. 1–10.
High Tech Ceramics, edited by P. Vincenzini, Elsevier Science Publishers B.V., Amsterdam, 1987—Printed in Netherlands, "Tensile Testing of Ceramic Materials—A New Approach", L. Hermansson, J. Adlerborn and M. Burstrom, pp. 1161–1167.
Axisymmetric Mechanical Analysis of Ceramic Heads for Total Hip Replacement, A. O. Andrisano, E. Dragoni and A. Strozzi, Proc. Instn. Mech. Engrs. vol. 204, 1990, pp. 157–167.
"Performance Comparison of Zirconia and Alumina Femoral Balls", H. Jung, I. Clarke, Y. Nasu, H. Yunoki, K. Makinouchi, T. Yanagida, The 15th Annual Meeting of the Society for Biomaterials, Apr. 28–May 2, 1989, p. 215.
"Fatigue Test of Zirconia and New Alumina Ceramic Hip Joint Heads", Koji Hyodo and Tetsuya Tateishi, Nippon Kikai Oakkai Tsujo Sokai Koenkai Koen Ronbunshu 70(4) 1993, pp. 885–886.
Prozyr, Bioceramic Expertise, "Yttria–Stabilized Ziconia Ceramic for Improved Hip Joint Head", J. M. Drouin and B. Cales, 7th International Symposium on Ceramics in Medicine, Turku, Finland, Jul. 1994, pp. 21–24.
Bioceramics vol., 3 (1992), Evaluation of Mechanical Properties of Zirconia Hip Joint, Tetsuya Tateishi, Koji Hyodo, Kazuo Kondo and Kazunori Miura, pp. 117–126.

* cited by examiner

FEMORAL PROSTHESIS EMPLOYING A SMALL CERAMIC BALL

Matter enclosed in heavy brackets [ ] appears in the original patent but forms no part of this reissue specification; matter printed in italics indicates the additions made by reissue.

TECHNICAL FIELD

The invention relates to a femoral prosthesis consisting of a metal rod and a femoral head or ceramic ball, preferably of zirconia, assembled by a conical sleeve fixing. The said femoral head is generally associated with a high density polyethylene (PE) acetabular cup.

STATE OF THE ART

When a total hip prosthesis is implanted, femoral heads are used which have a diameter of usually between 22.22 and 32 mm according to the surgical procedures employed. The materials used for producing the femoral heads are preferably metals such as stainless steel, the alloys Cr-Co-Mo, titanium, etc., or ceramics such as dense sintered alumina. Such a ceramic material offers demonstrated advantages of biocompatibility and a better friction coefficient vis-a-vis the high density PE than the metals. But taking into account its mechanical properties which are indeed high but insufficient its use is confined to large diameter femoral heads greater than or equal to 28 mm and to limited geometrical configurations (essentially a maximum neck gap of 4 mm for femoral heads of 28 mm diameter and of 8 mm for a diameter of 32 mm), in the event of its being desired to implant femoral prostheses consisting of a metal rod which, by a conical sleeve mounting, is attached to an alumina ball.

At the present time, if it is desired to implant prostheses having small diameter femoral heads fixed by a conical sleeve mounting on the femoral rod, then only metals are used with the disadvantages which they offer, particularly of less satisfactory friction properties vis-a-vis the high density PE cup.

Attempts have been made to use dense alumina femoral heads in order to take advantage of its better friction coefficient but taking into account their inadequate mechanical characteristics, such femoral heads cannot be used with a diameter which is smaller than 28 mm and which are assembled by a conical sleeve fitment on the femoral head without running the risk of the said head splitting.

Thus, various arrangements or modifications of the conical sleeve fitment have been proposed to overcome this problem. These arrangements generally consist in introducing a "stress deadener" into the conical sleeve fitment, between the metallic rod and the ceramic head.

It is possible, for example, to quote:

FR 2580170 (Flegeau) the use of an intermediate metal sleeve which by various means (particularly metallisation, brazing . . . ) is rendered rigid with a ceramic cup forming the femoral head, the said sleeve being engaged onto the frustoconical part of the femoral head;

FR 2610514 (Cuilleron) the pouring of a metal into a ceramic cup, providing in this solidified mass a recess in which the end of the femoral head is housed;

FR 2391711 (Sulzer) the use of a plastics sleeve inserted between the ceramic material and the metal.

All these solutions may provide answers to the problem of the mechanical strength of dense alumina femur heads but they are often difficult to use at the time when it is necessary to position the prosthesis and they do not generally satisfy the surgeon.

OBJECT OF THE INVENTION

That is why the applicants have sought to perfect a femoral prosthesis comprising an assembly by direct conical sleeve fitment between a femoral head of ceramic material and of small diameter of not more than 26 mm and a metal femoral rod without the help of intermediate members and/or other associated fixing means such as gluing, brazing, tenon, etc.

Thus, such a prosthesis is not subject to bursting when subjected to intense mechanical stresses, while it is at the same time simple to use and to place in position.

DESCRIPTION OF THE INVENTION

The invention is a femoral prosthesis consisting of a metal rod comprising at one of its ends a male frustoconical portion and a ceramic femoral head comprising at least one frustoconical blind recess, assembled by means of a conical sleeve fitment, characterized by the combination of the following means: the said head is of ceramic material, preferably dense stabilised zirconia, it has a diameter of not more than 26 mm, the total angle at the apex of the frustoconical blind recess used for the conical sleeve fitment is generally greater than 4°, the inlet diameter of the said truncated cone serving for conical sleeve fitment measured at the periphery of the femoral head is comprised between 8 and 14 mm and preferably between 10 and 11 mm.

The zirconia ceramic is obtained by sintering from a mixture of powdered zirconia and a stabilising agent known by a man skilled in the art, such as $Y_2O_3$, MgO, CaO, rare earth oxides . . . or their mixtures, the final content of $ZrO_2$ being generally greater than 95% (by weight). Either natural sintering is carried out after shaping and pressing cold, or a sintering under load of better still a sintering under isostatic load (HIP=Hot Isostatic Pressing) possibly including a presintering stage without a load.

Thus, a stabilised zirconia ceramic is obtained in the quadratic phase which can be used in accordance with the invention. *The quadratic phase is also known in the art as the tetragonal phase.* It is preferably that it should have at least the following physical properties:

- a specific mass in excess of 6 g/cu.cm or 98% of the theoretical density
- mean grain size (measured by electron scanning microscope using the method NF A 04102, which corresponds to ASTM E 112/82) less than or equal to 1 micron
- flexion breakage modulus 3 points better than 920 MPa (draft French Standards B41G Doc 12, now NF B 41-104, August 1989)
- [elasticity modulus (ASTM C 674 method) better than 220 GPa]

A sintered ceramic of another type, for example oxide, carbide, nitride, may likewise be used according to the invention so long as it has at least the mechanical characteristics of resistance to flexion[, Young's modulus,] and grain size previously indicated for zirconium and obviously so long as it satisfies the biocompatibility conditions required for the present application.

Advantageously, stabilised zirconia parts can be used which are obtained by HIP; for example, they have at least the following characteristics:

specific mass greater than 6 g/cu.cm
mean grain size less than 1 micron
resistance to flexion greater than 1600 MPa
[Young's modulus in excess of 220 GPa].

Similarly, other ceramics may be used which have at least the characteristics of one or other of the two aforementioned series.

The femoral head is generally spherical and has a diameter of at most 26 mm; the invention is particularly interesting for spheres with a diameter of 22.22 mm. The said head comprises at least one frustoconical blind recess the axis of which is preferably radial and the applicants have found that it was preferably necessary to use a total angle at the apex of at least 6° in order to obtain femoral prosthesis with a small diameter head (of at most 26 mm), of sufficiently high strength to be implanted with the minimum risk of breakage. It is generally considered that the femoral head has to be able to withstand a minimum loading of about 30 to 35 kN without damage or breakage. This rupture loading is measured according to the draft French Standards PR.S 90443 of Feb. 10, 1988, now NF S 90-443 of Sep. 28, 1988 in which an increasing force is applied to the femoral head mounted on the metal rod according to the axis of the assembly. A notable increase in solidity is obtained preferably by using an angle of about 10°.

Likewise, it is essential that simultaneously the inlet diameter of the cone should be as defined hereinabove, values in excess of 14 mm being in particular likely to increase significantly the risk of breakage of the femoral head.

The frustoconical blind recess has lateral walls which serve to ensure a self-locking assembly by conical sleeve fitment, being in contact with the walls of a corresponding metal male cone of preferably the same conicity, the said male cone situated at one end of a femoral rod of which the other end is implanted into the femur, is fitted with force and is therefore locked directly in the frustoconical recess.

The said blind frustoconical recess serving for a sleeve-like fitment opens out onto the surface of the said head either directly or through another slightly more open truncated cone, as will be seen hereinafter.

The metal femoral rod may be of an alloy of Ti, stainless steel, Cr-Co-Mo or any other metals or alloys used for making orthopaedic implants.

It is possible to optimise the mounting of the femoral head on the metal rod by any known means and particularly by the apparatus described in U.S. Pat. No. 4,964,869, issued Oct. 23, 1990, which matured from application Ser. No. 07/372, 753, filed Jun. 28, 1989 claiming priority based upon French Patent Application No. Jun. 28, 1989 claiming priority based upon French Patent Application No. 88-09042 filed Jun. 28, 1988 in which the contact between the male cone of the said rod and the female cone of the said head, ensuring assembly by a self-locking conical sleeve mounting, occurs only in a deep frustoconical zone of the blind recess in the ceramic head. *In the Examples of U.S. Pat. No. 4,964,869 ("the Auclair patent"), Examples 1,2,3, correspond to practical tests of ceramic balls with a diameter of 28 mm and a recess of a depth of 16.5 mm (i.e. the depth of the recess extends about 58.8% of the diameter of the balls), and examples 4 and 5 correspond to tests made on balls of sintered zirconium oxide of 28 mm diameter with a recess having a depth of 20 mm (i.e. the depth of the recess extends about 71.4% of the diameter of the balls).*

FIG. 1 shows a femoral prosthesis according to the invention. In it, reference numeral 1 denotes the femur

2 denotes the metal femoral rod, of which the end 3 is implanted into the femur and of which the frustoconical end 4 serves to assemble, by conical sleeve fitment, itself on the ceramic femoral head 5 of small diameter, at 6, the side wall of the frustoconical recess provided in the femoral head 5 which is in contact over its entire height with the lateral wall 7 of the male cone 4, and at 8 a space between the apex of the male truncated cone 4 and the bottom of the truncated recess provided in the head 5.

In this case, the blind recess consists of a single truncated cone which opens out directly onto the surface of the femoral head 5.

Figure 2:
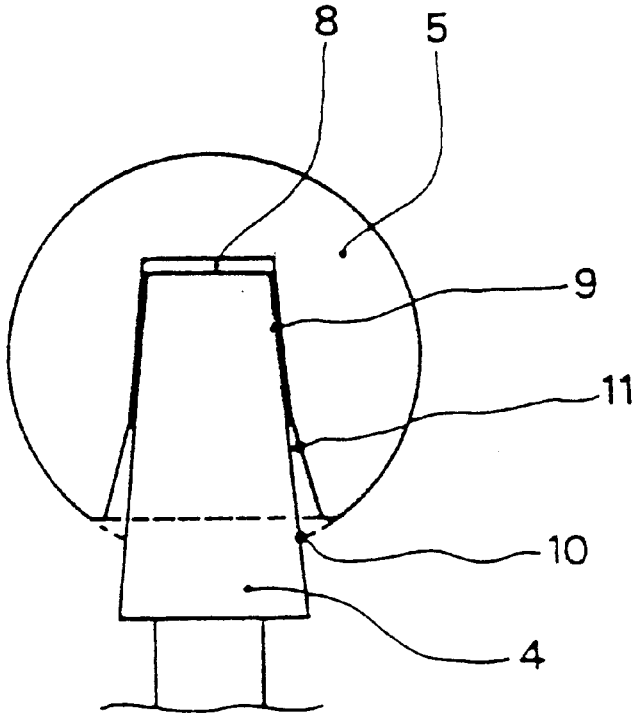
Figure 3:
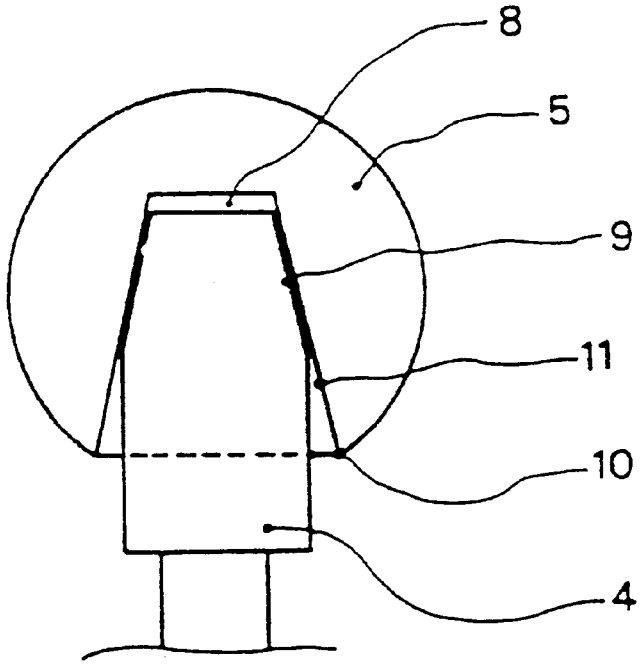

FIGS. 2 and 3 illustrate ways to optimise the conical sleeve fitment according to the invention, carried out according to the apparatus disclosed by French Application No. 88-09042 according to which the contact between the male and female cones takes place in a "deep" zone of the blind recess in the ceramic femoral head 5. *According to the Auclair patent, the depth of the bearing surface on which there is contact between the lateral surface of the recess and the corresponding surface of the peg in general comprises between 15% and 80%, preferably between 25 and 70%, of the total depth of the recess. Examples 2, 3 and 5 of the Auclair patent describe out of contact portions which extend into the head about 19.6%, 37.5% and 26.8% of the total head diameter, respectively.*

FIG. 2 shows that the zone of contact by self-locking conical sleeve fitting between the ceramic femoral head 5 and the metal femoral rod 4 occurs at 9 in the "deep" zone of the blind recess. The total angle at the apex according to the invention is that of this frustoconical contact zone. The non-contact zone 11 is situated towards the outside of the blind recess and is obtained in this case by a more flared machining of the femoral head 5. The entrance diameter 10 of the frustoconical blind recess where contact occurs is measured on the circle obtained by the intersection of the outer surface of the femoral head 5 and the extension of the truncated contact cone 9.

In FIG. 3, the contact zone 9 is still situated in the deep zone of the blind recess. The non-contact zone 11 is obtained in this case by a relief machining of the corresponding part of the male cone 4 on the metal femoral rod. The diameter at the entrance 10 to the frustoconical blind contact recess is likewise measured on the circle obtained by intersection of the said frustoconical recess with the outer surface of the femoral head.

EXAMPLES

To illustrate the interest of the invention, rupture tests were carried out on the ceramic femoral head of various prostheses according to draft Standard PRS 90443. Femoral hip prosthesis parts with an attached head: specifications for the head and for the male part of the socket fitment, now NF S 90-443 of Sep. 28, 1988. The principle of the test resides in applying a load to the ceramic head according to the axis of assembly until the said head is destroyed.

EXAMPLE 1

Prostheses were prepared using a femoral head consisting of dense alumina; the mechanical characteristics of this alumina are in accordance with the Standard ASTM F603 or ISO 6474.

To illustrate the problems raised by adapting this material to the production of certain types of femoral prosthesis, small diameter (26 mm) alumina femoral heads were mounted on a metal femoral rod using a conical sleeve fitting of the type shown in FIG. 1 (contact between a male cone and a blind recess over all the walls of the said blind recess in the femoral head), using the same angle for the blind recess and the male cone.

The geometrical characteristics are as follows:

diameter of the femoral head: 26 mm total angle at the apex of the recess: 6° diameter at the entrance to the cone: 14 mm

The tests carried out produced a break at 25 kN, a level deemed insufficient for a no-risk implant.

EXAMPLE 2

In this example which is intended to illustrate the invention, the femoral heads are of dense sintered zirconia obtained by natural sintering, the quality of which complies with the characteristics given earlier in the description. The femoral heads have a diameter of 26 mm and the conical sleeve fitting is identical to that in Example 1. The results of the test are given in the following Table:

| Tests (26 mm) | Angle at apex (*) | Diameter at entrance to cone (mm) | Breaking load (kN) |
|---|---|---|---|
| 1 | 6 | 14 | 43 |
| 2 | 6 | 12 | 50 |
| 3 | 10 | 11 | 61 |

One can see that according to the invention Test No. 1 shows an improved breaking load which means that the prosthesis can be implanted, the breaking resistance fairly clearly exceeding the limit threshold of 30 to 35 kN.

One can likewise see a particularly improved result with Test No. 3 (10° angle and cone entrance diameter of 11 mm).

EXAMPLE 3

This example likewise illustrates the invention. In these tests, the femoral head has a diameter of 22.22 mm and the conical sleeve fitting is of the same type as described with reference to FIG. 2: contact of the male cone on only a part of the walls of the blind recess by flaring the front part of the said recess.

Two types of ceramics were used: dense zirconia identical to that in Example 2 obtained by natural sintering, zirconia obtained by H.I.P. having the corresponding characteristics given in the description.

The results obtained are as follows:

| Tests (22.22 mm) | Angle at apex (*) | Diameter at entrance to cone (mm) | Breaking load (kN) |
|---|---|---|---|
| 4 (naturally sintered zirconia) | 10 | 10 | 82 |
| 5 (HIP zirconia) | 10 | 10 | 120 |

These tests show that even with small diameter femoral heads, very high breaking loads are obtained according to the invention.

Thus, the combined characteristics of the invention make it possible to use small diameter femoral heads (at most 26 mm and in particularly 22.22 mm) to produce femoral prostheses by conical sleeve fitting on a metal rod, which have no risks of breaking after implant, while such a result is not possible with prior art femoral heads of dense alumina.

We claim:

1. A femoral prosthesis comprising:

a metal rod comprising a first end adapted to be implanted in a femur and a second frustoconical end having a total angle greater than 4°, a ceramic femoral head comprising a substantially spherical body with an outer surface having a diameter which is not more than [26] *22.22* mm and made of [a ceramic material] *tetragonal zirconia* having a mean grain size not more than 1 micrometer, *and* a 3 points flexion breakage modulus better than 920 MPa [and an elastically modulus greater than 220 GPa], a blind-ended recess being provided in said body and comprising an inwardly converging frustoconical shaped recess having a total angle substantially the same as said total angle of said frustoconical end of said metal rod, said frustoconical shaped recess intersecting said outer surface of said body in a circle having an entrance diameter between about 8 and about 14 mm, said frustoconical end of said metal rod being force-fitted in said blind-ended recess, *said prosthesis having a rupture load of between 82 kN and 120 kN.*

[2. A femoral prosthesis according to claim 1, wherein said ceramic material comprises stabilized dense zirconia.]

[3. A femoral prosthesis according to claim 2, wherein said ceramic material contains at least 95%, by weight, of $ZrO_2$.]

[4. A femoral prosthesis according to claim 1, wherein said ceramic material is a Hot Isostatic Pressing sintered material.]

[5. A femoral prosthesis according to claim 1, wherein said body has a specific mass at least equal to 98% of the theoretical density of said ceramic material.]

[6. A femoral prosthesis according to claim 5, wherein said ceramic material has a 3 points flexion breakage modulus greater than 1600 MPa.]

[7. A femoral prosthesis according to claim 1, wherein said entrance diameter is between about 10 and about 11 mm.]

[8. A femoral prosthesis according to claim 7, wherein said entrance diameter is substantially 10 mm.]

[9. A femoral prosthesis according to claim 1, wherein said total angles of said frustoconical end and said frustoconical shaped recess are at least equal to 6°.]

[10. A femoral prosthesis according to claim 9, wherein said total angles are about 10°.]

[11. A femoral prosthesis according to claim 1, wherein said body of said ceramic femoral head has a diameter which is at least about 22.22 mm.]

[12. A femoral prosthesis according to claim 1, wherein said frustoconical end and the surfaces defining said blind-ended recess are only in contact along an inner portion thereof, said frustoconical end and said blind-ended recess being out of contact near said outer surface of said femoral head.]

[13. A femoral prosthesis according to claim 2, wherein said ceramic material is a Hot Isostatic Pressing sintered material.]

[14. A femoral prosthesis according to claim 2, wherein said ceramic material has a specific mass of at least 6 g/cu.cm.]

[15. A femoral prosthesis according to claim 2, wherein said entrance diameter is between about 10 and about 11 mm.]

[16. A femoral prosthesis according to claim 2, wherein said total angles of said frustoconical end and said frustoconical shaped recess are at least 6°.]

[17. A femoral prosthesis according to claim 16, wherein said total angles are about 10°.]

[18. A femoral prosthesis according to claim 2, wherein said body of said ceramic femoral head has a diameter which is at least about 22.22 mm.]

[19. A femoral prosthesis according to claim 18, wherein said entrance diameter is about 10 mm and said total angles of said frustoconical end and said frustoconical shaped recess are about 10°.]

[20. A femoral prosthesis according to claim 18, wherein said ceramic material is Hot Isostatic Pressing sintered.]

[21. A femoral prosthesis according to claim 18, wherein the surface defining said blind-ended recess and said frustoconical end are out of contact near said outer surface of said femoral head.]

* * * * *